United States Patent [19]
Wicks et al.

[11] Patent Number: 6,001,822
[45] Date of Patent: Dec. 14, 1999

[54] ANTIPARASITIC FORMULATIONS

[75] Inventors: Stephen R. Wicks; Edward Davison, both of Kent, United Kingdom

[73] Assignee: Pfizer Inc., New York, N.Y.

[21] Appl. No.: 07/879,083

[22] Filed: May 1, 1992

Related U.S. Application Data

[63] Continuation of application No. 07/505,815, Apr. 6, 1990.

[30] Foreign Application Priority Data

Apr. 11, 1989 [GB] United Kingdom .................. 8908071

[51] Int. Cl.$^6$ ...................... A61K 31/695; A61K 31/215
[52] U.S. Cl. ............................................. 514/63; 514/531
[58] Field of Search ....................... 514/63, 531

[56] References Cited

U.S. PATENT DOCUMENTS

| | | | |
|---|---|---|---|
| 4,389,397 | 6/1983 | Lo et al. ................................. | 424/180 |
| 4,859,657 | 8/1989 | O'Sullivan et al. ..................... | 514/63 |
| 4,871,719 | 10/1989 | Maienfisch ............................ | 514/63 |
| 4,916,120 | 4/1990 | Röban et al. .......................... | 514/30 |
| 4,916,154 | 4/1990 | Asato et al. ........................... | 514/450 |

FOREIGN PATENT DOCUMENTS

| | | |
|---|---|---|
| 146414 | 6/1985 | European Pat. Off. . |
| 214731 | 3/1987 | European Pat. Off. . |
| 2166436 | 5/1986 | United Kingdom . |
| 2176182 | 12/1986 | United Kingdom . |

*Primary Examiner*—Russell Travers
*Attorney, Agent, or Firm*—Peter C. Richardson; Gregg C. Benson; A. Dean Olson

[57] ABSTRACT

A parenteral formulation for 25-cyclohexyl-avermectin Bl, compound (I), which is effective against both internal and external parasites, is well tolerated by animals on both subcutaneous and intramuscular administration and is compatible with conventional injection equipment.

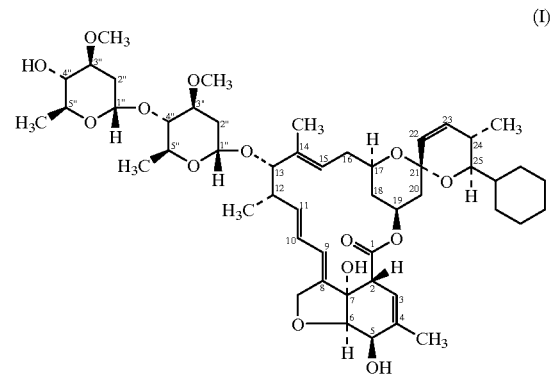

The solution comprises compound (I), in a solvent consisting of from 50 to 95% by volume of sesame oil with the remainder ethyl oleate.

10 Claims, No Drawings

ANTIPARASITIC FORMULATIONS

This is a continuation of application Ser. No. 07/505,815, filed on Apr. 6, 1990.

TECHNICAL FIELD

This invention concerns the preparation of parenteral formulations of the compound known as 25-cyclohexyl-avermectin B1 of formula (I).

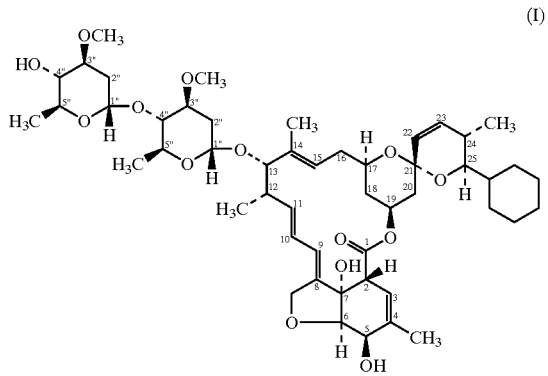

This above compound, 25-cyclohexyl-avermectin B1, is a member of the avermectin family, described and claimed in European Patent publication 0214731. The avermectins are highly active antiparasitic agents having particular utility as anthelmintics, ectoparasiticides, insecticides and acaricides.

Antiparasitic agents are most conveniently administered to animals by using parenteral, subcutaneous or intramuscular formulations. Water is generally a convenient liquid for injection, but avermectins have a very low solubility in water and simple aqueous solutions are too dilute to be usable. Certain avermectins can be solubilized in water using surface active agents as solubilisers and suitable organic co-solvents to form a micellar solution as described in U.S. Pat. No. 4,389,397. However, these formulations do not provide doses of active compounds sufficient to remove satisfactorily both internal and external parasites of animals.

European Patent publication 146414 describes co-solvent solutions of avermectins, in a mixture of glycerol formal and propylene glycol or in propylene glycol containing a minor amount of water, for parenteral use. However, propylene glycol is known to cause irritation on subcutaneous or intramuscular injection. Additionally, minor amounts of water in these formulations may cause hydrolytic degradation of the avermectin.

Such formulations, which comprise water-miscible organic solvents for the avermectin, tend to produce unwanted local precipitation of the avermectin at the injection site. This may result in irritation and swelling at the injection site and in inefficient and inconsistent antiparasitic efficacy.

Indeed, the commercially available antiparasitic agent, "Ivomec injectable for cattle", a co-solvent formulation of an avermectin known as ivermectin, is only suitable for subcutaneous use and may cause irritation and swelling at the injection site.

An alternative method of providing an injectable solution of an avermectin is to dissolve the avermectin in a pharmaceutically acceptable oil. The use of arachis (peanut) and cottonseed oils, and also ethyl oleate, as solvents for certain avermectins is disclosed in British patent publication 2166436. However, arachis oil and cottonseed oil do not provide a solution having at least a 1% w/v concentration of compound I, as is generally required for a veterinary product. Veterinary formulations are commonly used or stored on farms at low temperatures, down to 4° C. or even lower, and even if the avermectin is sufficiently soluble in the oil at normal room temperature it may precipitate or form a supersaturated solution, on exposure to cold conditions and thus become unusable. Pure ethyl oleate, and mixtures of oils containing a major proportion of ethyl oleate, attack certain plastics or rubber components of commonly used veterinary syringes to an unacceptable extent.

European Patent Application 285561 mentions pure sesame oil as a possible solvent for a different group of compounds, the milbemycins. In comparative viscosity and syringeability studies it has been found that pure sesame oil has a viscosity which is too high to allow its use as a solvent for injection using conventional veterinary syringe equipment. For this reason, pure sesame oil cannot be used as an injectable solvent under practical field conditions.

SUMMARY OF THE INVENTION

The present invention is intended to provide a parenteral formulation for compound (I) which is effective against both internal and external parasites, is well tolerated by animals on both subcutaneous and intramuscular administration and is compatible with conventional injection equipment.

According to the invention, there is provided a solution of 25-cyclohexyl-avermectin B1, compound (I), in a solvent consisting of from 50 to 95% by volume of sesame oil with the remainder ethyl oleate.

Another aspect of this invention relates to a process for making the above described formulation which comprises dissolving compound I in a solvent consisting of from 50% to 95% by volume of sesame oil with the remainder ethyl oleate.

Yet another aspect of this invention is directed to a method of combatting parasitic infections or infestations, both internal and external including parasitic conditions in animals and humans, which comprises administering by injection an antiparasitic effective amount of the above described solvent solution to the afflicted animal or human.

DETAILED DESCRIPTION OF THE INVENTION

The formulations according to the invention are monophase solutions and are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, *Dirofilaria* in dogs and various parasites which can infect humans including gastrointestinal parasites such as *Ancylostoma, Necator, Ascaris, Strongyloides, Trichinella, Capillaria, Trichuris, Enterobius* and parasites which are found in the blood or other tissues and organs such as filiarial worms and the extra intestinal stages of *Strongyloides* and *Trichinella*.

The formulations of the invention are also of value in treating ectoparasite infections including in particular anthropod ectoparasites of animals and birds such as ticks, mites, lice, fleas, blowfly, biting insects and migrating dipterous larvae which can affect cattle and horses.

It has been found, unexpectedly, that formulations according the invention show properties which are superior to the prior art formulations mentioned above, in that they show little or no irritation at the injection site when administered to animals by subcutaneous or intramuscular injection, are suitable for use in commonly used standard syringes, and give consistent antiparasitic efficacy.

A further advantage of the solutions of the invention is that, as the formulation vehicle contains esters of unsaturated acids, the avermectin is protected from air oxidation during prolonged storage.

The solutions of the invention may be prepared simply by dissolving compound (I) in the sesame oil ethyl oleate mixture and sterilising and packaging for administration in a conventional manner.

The preferred solvent mixture consists of from 75 to 90% of sesame oil by volume with the remainder ethyl oleate.

The preferred content of avermectin for subcutaneous or intramuscular injection is from 1 to 30 mg/ml, most preferably about 10 mg/ml.

Formulations according to the invention are described by way of illustration in the following Examples.

EXAMPLES

Solutions of 25-cyclohexyl-avermectin B1 in the oil formulations were made and tested by the methods given below.

Example 1

The following ingredients were used to prepare an injectable solution containing 10 mgs of compound I in 1 ml of a nominal 90/10 mixture of sesame oil and ethyl oleate:

| | |
|---|---|
| Compound I | 10 mg |
| Ethyl oleate | 0.1 ml |
| Sesame oil | to 1.0 ml |

The ethyl oleate and sesame oil were mixed and heated to 80° C., whilst purging with nitrogen. Compound I is then added to the hot oils until dissolved and the resulting solution rapidly cooled and the volume adjusted to 1 ml with sesame oil, if required. This final solution was sterilised by membrane filtration and packaged aseptically.

Example 2

Using the method of example 1, the following ingredients were used to prepare an injectable solution containing 10 mgs of compound I in 1 ml of a nominal 50/50 mixture of sesame oil and ethyl oleate:

| | |
|---|---|
| Compound I | 10 mg |
| Ethyl oleate | 0.25 ml |
| Sesame oil | to 1.0 ml |

Example 3

Using the method of example 1, the following ingredients were used to prepare an injectable solution containing 10 mgs of compound I in 1 ml of a nominal 75/25 mixture of sesame oil and ethyl oleate:

| | |
|---|---|
| Compound I | 10 mg |
| Ethyl oleate | 0.25 ml |
| Sesame oil | to 1.0 ml |

Example 4

The efficacy of compound I against ectoparasites was determined using a modification of the method described by L G Cramer et al., in *Vet. Record,* (1988), 122, 611–612.

Compound I was administered to two groups of cattle by subcutaneous injection at a dose of 200 µg/kg on day 0. Group A received compound I in an aqueous micelle formulation according to U.S. Pat. No. 4,389,397 containing 2.5 mg of compound I, 120 mg of Tween 80 (Registered Trade Mark), 200 mg of glycerol formal, about 10 mg of benzyl alcohol and the remainder water per ml of formulation. Group B were treated with compound I in the formulation of example 1. The treated groups, together with a control for each treatment were then seeded with *Boophilus microplus* larvae on days 0, 2 and 4 and the ticks allowed to develop into adults. Resulting engorged adult female ticks were collected between days 21 and 32 and the mean daily counts recorded as shown in Table 1.

TABLE 1

Mean Daily counts of female B. microplus ticks collected

| Day | Micelle Formulation | Untreated Control | Formulation Example 1 | Untreated Control |
|---|---|---|---|---|
| 21 | 0 | 287 | 0 | 0 |
| 22 | 0 | 651 | 0 | 324 |
| 23 | 0 | 879 | 0 | 996 |
| 24 | 0 | 753 | 0 | 1507 |
| 25 | 16 | 554 | 0 | 663 |
| 26 | 76 | 267 | 0 | 852 |
| 27 | 85 | 48 | 0 | 329 |
| 28 | 36 | 10 | 8 | 35 |
| 29 | 28 | 5 | 15 | 19 |
| 30 | 16 | 0 | 3 | 1 |
| 31 | 0 | 0 | 3 | 1 |
| 32 | 0 | 0 | 1 | 0 |
| Totals | 257 | 3454 | 30 | 4727 |

Treatment with formulation example 1 both delayed the production of adult female ticks and resulted in fewer ticks collected.

Example 5

The toleration of avermectin formulations was assessed following injection into the semimembraneous muscle of cattle. Animals were humanely sacrificed at 7 and 14 days post-treatment and the injection sites, with surrounding tissue, removed. Tissues were examined for gross pathology and injection site lesions were evaluated using the scoring system described below.

0=Normal, no visible lesion

1=Light scar

2=Heavy scar

3=Encapsulated debris<1.0cm$^3$

4=Encapsulated debris>1.0<2.5cm$^3$

5=Encapsulated debris>2.5cm$^3$

Scores 0, 1 and 2 are considered acceptable. Scores greater than 2 have encapsulated debris. Compound I in formulations of examples 1 and 2 was administered to cattle by intramuscular injection at a dose of 200 µg/kg. Injection site toleration was compared with that of the co-solvent formulation of the antiparasitic agent, ivermectin (Trademark; Ivomec for cattle) given at the same dose and by the same route.

TABLE 2

Comparison of intramuscular injection site toleration scores

| Treatment | Day | Number of Animals | Average Score |
|---|---|---|---|
| Formulation example 1 | 7 | 5 | 0.4 |
|  | 14 | 10 | 0.0 |
| Formulation example 2 | 7 | 5 | 0.4 |
|  | 14 | 10 | 0.0 |
| Ivomec | 7 | 4 | 3.75 |
|  | 14 | 8 | 2.75 |

Compound I in formulation examples 1 and 2, was well tolerated with only a few minor lesions at 7 days post-injection; resolving completely by 14 days. In contrast, Ivomec given by intramuscular injection was poorly tolerated at 7 days with encapsulated debris still visible 14 days post-injection.

We claim:

1. A pharmaceutical composition comprising a solution of compound (I) in a solvent consisting of from 50 to 95% by volume of sesame oil with the remainder ethyl oleate.

2. The composition as recited in claim 1 wherein said solvent consists of from 75 to 90% of sesame oil by volume with the remainder ethyl oleate.

3. The composition as recited in claim 1 wherein said solution contains from 1 to 30 mg/ml of 25-cyclohexyl-avermectin B1.

4. The composition as recited in claim 1 wherein said solution contains about 10 mg/ml of 25-cyclohexyl-avermectin B1.

5. A method of treating both internal and external helminth, insect or acari infections in animals and humans comprising administering by injection a helminth-, insect- or acari-treating effective amount of a solution of compound (I) in a solvent consisting of from 50 to 95% by volume of sesame oil with the remainder ethyl oleate to said animal or human.

6. The method as recited in claim 5 wherein said solvent consists of from 75 to 90% of sesame oil by volume with the remainder ethyl oleate.

7. The method as recited in claim 6 wherein from 1 to 30 mg/ml compound I is injected subcutaneously or intramuscularly.

8. The method as recited in claim 7 wherein the dosage is about 10 mg/ml.

9. An injectable pharmaceutical composition consisting essentially of a solution of compound (I) in a solvent of from 50 to 95% by volume of sesame oil with the remainder ethyl oleate.

10. The composition as recited in claim 9 wherein said solvent consists of from 75% to 90% of sesame oil by volume with the remainder ethyl oleate.

* * * * *

UNITED STATES PATENT AND TRADEMARK OFFICE
CERTIFICATE OF CORRECTION

PATENT NO. : 6,001,822
DATED : December 14, 1999
INVENTOR(S) : Stephen R. Wicks and Edward Davison It is certified that error appears in the above-identified patent and that said Letters Patent is hereby corrected as shown below:

<u>Column 5,</u>
Line 26, "1. A pharmaceutical" should read -- 1. An injectable pharmaceutical --

Signed and Sealed this

Twenty-ninth Day of June, 2004

JON W. DUDAS
*Acting Director of the United States Patent and Trademark Office*